United States Patent [19]

Banker et al.

[11] Patent Number: 5,674,507
[45] Date of Patent: Oct. 7, 1997

[54] LOW CRYSTALLINITY CELLULOSE EXCIPIENTS

[75] Inventors: Gilbert S. Banker, Iowa City, Iowa; Shi Feng Wei, Bloomfield, N.J.

[73] Assignee: Biocontrol, Inc., Iowa City, Iowa

[21] Appl. No.: 428,865

[22] Filed: Apr. 25, 1995

Related U.S. Application Data

[62] Division of Ser. No. 990,621, Dec. 14, 1992, Pat. No. 5,417,984.

[51] Int. Cl.$^6$ ............................ A61K 7/00; A61K 9/14
[52] U.S. Cl. ...................... 424/401; 424/488; 424/499; 424/464; 8/127.1; 536/56; 514/951; 514/960
[58] Field of Search ................... 424/401, 195.1, 424/488, 499, 464; 8/127.1; 536/56; 514/951, 960

[56] References Cited

U.S. PATENT DOCUMENTS

| | | | |
|---|---|---|---|
| 2,978,446 | 4/1961 | Battista et al. | 260/212 |
| 3,146,170 | 8/1964 | Battista | 167/85 |
| 4,058,411 | 11/1977 | Bellamy et al. | 127/37 |
| 4,357,467 | 11/1982 | Sachetto et al. | 836/56 |
| 4,575,376 | 3/1986 | Shah | 8/116.1 |
| 4,919,681 | 4/1990 | Tyler | 8/116.1 |
| 5,244,734 | 9/1993 | Okuma | 536/57 |

*Primary Examiner*—Sallie M. Gardner
*Attorney, Agent, or Firm*—Zarley, McKee, Thomte, Voorhees, & Sease

[57] ABSTRACT

A rapid method to prepare low crystallinity cellulose (crystallinity 15–45% of polymerization 35–150), suitable for use as a direct compression excipient (e.g., binder, disintegrant, and diluent) in pharmaceutical solid dosage forms design and as a bodying and/or film forming agent in the development of sustained- and/or film forming agent in the development of sustained- and/or controlled-release pharmaceutical (topical and transdermal products), cosmetics, agricultural, personal care and like products, is provided by reacting cellulose materials with 85% or higher weight percentage phosphoric acid under controlled sequenced temperature conditions that involve treatment first at room temperature for an hour and then at 50°–55° C. for 3–6 hours, followed by separating by a precipitation method, and subsequently isolating as a powder or converting into a head or hydrated form.

10 Claims, 12 Drawing Sheets

LOW CRYSTALLINITY CELLULOSE EXCIPIENTS

This is a divisional of application Ser. No. 07/990,621 filed on Dec. 14, 1992, now U.S. Pat. No. 5,417,984.

BACKGROUND OF THE INVENTION

Cellulose is the most abundant natural polymer. All forms of plant life contain cellulose. Because of its nearly ubiquitous distribution in nature, and human kinds' long exposure to cellulose, cellulose and its derivatives are generally recognized as the safest and most acceptable polymer class for use in food and pharmaceutical products. In its naturally occurring form, cellulose exists as a fibrous structure composed of arrays of long chains of cellulose molecules held together by van der Waal forces and interchain hydrogen bonds. The chemical structure of cellulose consists of repeating units of β-D glucopyranose rings linked together by β-1,4-glycosidic linkages. Depending on the degrees of order of arrangement and hydrogen bonding between cellulose chains, the crystallinity of the cellulose may range from 50% to 90%. The crystallinity of native cellulose is about 70% (P. H. Hermans and A. Weidinger, *J. Poly. Sci.*, IV, 135,(1949)). The amorphous regions in the structure can result from damage during processing of pulp, from different chain bonding order (i.e., occurrence of β-1, 6-linkage instead of the regular β-1,4-glycosidic bond) or as a result of natural imperfections. The degree of polymerization of cellulose may range from 1,000 to 10,000, depending on its source.

The reactions of cellulose with mineral acids to prepare non-fibrous, low molecular weight (i.e., low degree of polymerization) cellulose products suitable for use in food, cosmetics, pharmaceutical, and like products, have been extensively studied. The reactivity of cellulose towards acids depends on the crystallinity of the cellulose source, acid concentration, and the reaction temperature and duration. Several products with varying degrees of crystallinity and polymerization have been prepared. Battista (U.S. Pat. Nos. 2,978,446 and 3,146,170) disclose the preparation of level-off cellulose products suitable for the manufacture of microcrystalline cellulose—the most commonly and widely used direct compression excipient for pharmaceutical solid dosage form design, by reacting a cellulose material with 2.5N hydrochloric acid at boiling temperature for 15 minutes. According to the invention, the products produced are highly crystalline in nature. The level-off degree of polymerization values of products prepared from native fibers range between 200 and 300, whereas those prepared from regenerated cellulose lie in the range of from 15 to 60, and products prepared from alkali swollen natural forms of cellulose are in a degree of polymerization range between 60 and 125. Similar manufacturing procedures, to that described above, are described in German Patent DAS 1,123,460, using viscose cellulose as the starting cellulose source, and in Austrian Patent No. 288,805. The use of gaseous HCl, at temperatures below 40° C., without solvent, to prepare the cellulose precursor for microcrystalline cellulose, is disclosed in (East) German patent DD 71,282.

Ellefsen et al., in Norsk Skog Industri, 1959, p. 411, describe the preparation of crystalline cellulose products by dissolving the starting cellulose source in 38–40.3% concentrated hydrochloric acid at 20° C., followed by precipitating with water. In U.S. Pat. No. 4,357,467, a similar procedure to the foregoing, using 37–42% HCl acid at 30°–50° C., is employed to prepare cellulose products having substantially reduced crystallinity (17–83%), and a low degree of polymerization (10–200). Compared to native and regenerated cellulose, the low crystallinity cellulose products show improved dispersibility in water, increased compatibility with basic compounds such as starches, proteins, and lipids, and are useful as excipients in the preparation of tablets and confectionery products.

Greidinger et al (U.S. Pat. No. 3,397,198) disclose the preparation of an amorphous degraded cellulose by treating a cellulose material with 65–75% sulfuric acid at a temperature of 35°–45° C. for a period of no longer than 10 minutes. The amorphous product is suitable for use in cleaners, cosmetic preparations, foodstuffs or as a filler for materials such as plaster-of-paris or adsorbents.

V. M. Brylyakove (SU Patent 4266981) describe the preparation of microcrystalline cellulose utilizing 3–5% nitric acid, sulfuric acid or hydrochloric acid and a fatty acid ($C_{10-20}$) at 96°–98° C. The fatty acid enhances the efficiency of the process.

Other references that can be cited, pertinent to the preparation of microcrystalline cellulose, are: CA 111 (8) 59855w; CA 111 (8) 59787a; CA 108 (18) 152420y; CA 104 (22) 188512m; CA 104 (24) 209374K; CA 104 (24) 193881C; CA 99 (24) 196859y; CA 98 (12) 95486y; CA 94 (9) 64084d; and CA 85 (8) 48557u.

The interaction of cellulose with phosphoric acid has been the subject of several publications. S. M. Hudson and J. A. Cuculo, *Macromol. Sci. -Rev. Macromol. Chem.*, C18, 6–7 (1980) and J. O. Warwicker, in Cellulose and Cellulose Derivatives," N. M. Bikales and L. Segal, eds., Wiley, New York, N.Y. (1971), Vol. V, Part IV, p. 325–79, describe that the swelling and/or dissolution of cellulose in phosphoric acid depend(s) on the concentration of the acid. In concentration range between 71–80%, the swelling of cellulose is rapid. Further increases in the concentration causes dissolution of the cellulose. According to Hudson and Cuculo, the dissolution of cellulose is incomplete when the acid solution contains higher than 85% and less than 92% phosphoric acid. S. N. Danilov and N. F. Gintse, *Zh. Obsch. Khim.*, 26, 3014 (1956), describe that the cellulose dissolves more readily with increasing temperature, with a maximum dissolution rate at 40°–50° C.

Bellamy and Holub (U.S. Pat. No. 4,058,411) disclose the use of 80–85% phosphoric acid for the decrystallization of cellulose. According to the invention, the starting cellulose source, having particles about one millimeter in length and diameter, is reacted with phosphoric acid at room temperature, with or without the presence of a surfactant, for a prolonged period until a gel is formed. The product is then precipitated from the gel using an aqueous solution of tetrahydrofuran. The amorphous product can be used as a source of glucose or as a substrate for microbial production of antibiotics and other metabolites, single cell proteins and industrial alcohol.

In Swiss Patent No. 79,809, a method is described for the depolymerization of cellulose using a mixture of hydrochloric acid and sulfuric acid or phosphoric acid (25–35%) at temperatures below 50° C., is provided. There is, however, no mention of the crystallinity of the product in the disclosure.

We have found that the treatment of cellulose with phosphoric acid, under controlled sequenced temperature conditions, provides a rapid method of preparing low crystallinity cellulose products that are suitable for use as excipients in cosmetic, food, pharmaceutical, and like products.

Accordingly, the primary objective of this invention is to provide a rapid method for converting fibrous cellulose material to useful low crystallinity cellulose excipients using phosphoric acid.

A further objective of the present invention is to provide new low crystallinity cellulose excipients suitable for use in cosmetic, pharmaceutical, personal care, and like products.

Still another objective of this invention is to provide a bodying agent and/or film forming agent composed of hydrated low crystallinity cellulose.

These and other objectives of the present invention will be more apparent from the discussion that follows.

SUMMARY OF THE INVENTION

The present invention provides new low crystallinity cellulose (LCC) excipients, namely, low crystallinity powder cellulose (LCPC), low crystallinity bead cellulose (LCBC), and low crystallinity hydrated cellulose (LCHC), suitable for use in cosmetic, pharmaceutical, personal care, and like products, prepared by reacting a cellulose material with 80% or higher weight percentage phosphoric acid, (preferably 85% to 99%) first at room temperature (i.e. from 15° C. to 30° C.) for up to about an hour, and then at 50°–60° C. for a period of time (typically 3–6 hours), sufficient to dissolve the cellulose in the acid. As used herein, the term low crystallinity cellulose is intended to refer to a white solid material that precipitates when water or an appropriate organic solvent is combined with the above reaction solution, which can then be readily isolated as a powder (LCPC), or converted into a bead form (LCBC) or into an aqueous colloidal dispersion (LCHC). The degree of crystallinity of the products, prepared under the conditions of this invention, ranges between about 15% and 45%, and the degree of polymerization values range from about 35 to 150.

Therefore, the present invention also provides a rapid method whereby cellulosic materials, such as cotton linters, purified cotton papers, α-cellulose, purified wood pulp, microcrystalline cellulose, or like materials, can be readily converted into a low crystallinity cellulose product.

Owing to the greatly reduced degree of crystallinity and submicron particle size (0.2–0.5 μm), the LCC products show high enthalpy of immersion (LCPC:-31.01 cal/g; LCBC:-19.66 cal/g) and large surface area (LCPC: 2.45 m²/g; LCBC: 2.33 m²/g). Avicel®PH-101 (FMC Corporation), the most commonly and widely used microcrystalline cellulose product, has a surface area of only 1.40 m²/g and shows an enthalpy of immersion value of only −16.74 cal/g. LCPC shows strong bonding/binding properties on compression, and plastic deformations with a lower mean yield pressure upon compression (82 MPa versus. 125 MPa for Avicel®PH-101), which explains its superiority as a binder in tablets. The LCBC serves as an excellent disintegrate in tablets because of its capillary structure, that allows for rapid penetration for water, for water interactions. Other factors contributing to its superior disintegrating properties include a lack of entanglement or interlocking between bead particles, the release of stored elastic mechanical energy as the compressed but intact beads expand as the tablets disintegrate, the strong affinity of bead particles for interactions with water, and the release of high heat of immersion.

LCHC can be used as a novel film forming system, and/or as a bodying agent or as a carrier or co-carrier for a wide range of bioactive compounds or cosmetic compounds in systems for application to skin or hair, thereby producing substantive, controlled and/or sustained-release topical and transdermal formulations that have superior cosmetic and elegance features. Such formulations may be devoid of fats, waxes, oils, or surfactants, thereby producing natural, hypoallergenic and non-irritating topical systems. The present LCHC material can also carry bioactive materials to plant surfaces, again producing substantive, biocompatible, controlled and/or sustained release systems, which have the added advantage of being ultimately biodegradable in the environment.

DETAILED DESCRIPTION OF THE INVENTION

Figure 1:
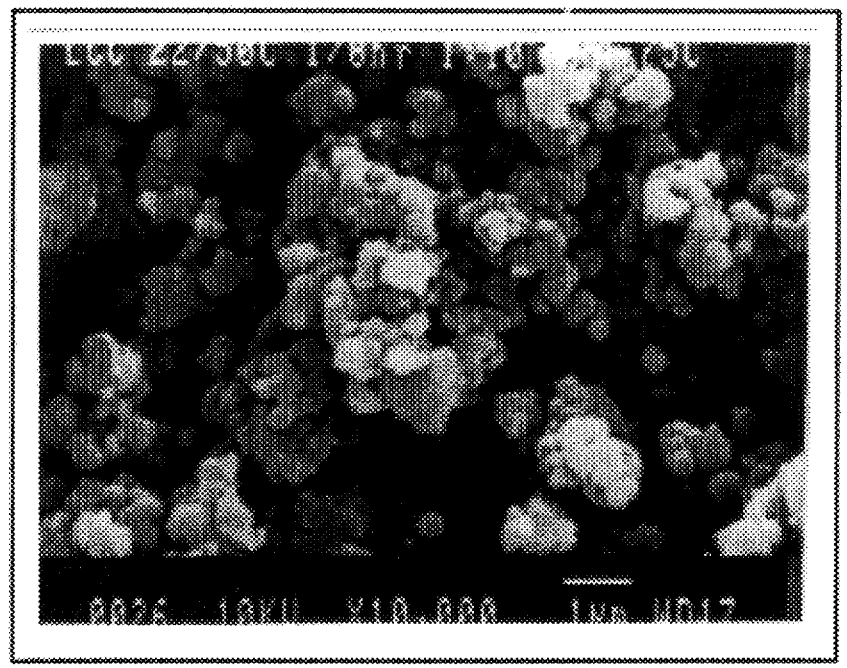
FIG. 1 is a scanning electron micrograph of low-crystallinity powdered cellulose (LCPC) of this invention.

According to the invention, the new low crystallinity cellulose product, readily convertible into powder, bead and hydrated forms, is prepared by reacting a cellulose material with 80% or higher, preferably 85% or higher, weight percentage phosphoric acid, first at room temperature (i.e. 15° C. to 20° C.) for about an hour, and then at a temperature of 45°–75° C., preferably 50°–60° C., for about 2 to 10.5 hours, preferably about 3–6 hours. It is important that the phosphoric acid be present in a sufficient quantity to initially uniformly impregnate the cellulose material, and that the reaction temperature sequence be observed. Although the minimum weight-to-volume ration of cellulose to phosphoric acid that can be used is about 1:2, it is preferred, for the purpose of this invention, to employ a ratio of 1:2–1:20 most preferably 1:3 to 1:10. The higher ratios (i.e., higher than 1:10) of cotton linters to phosphoric acid can also be used, but are wasteful of acid and hence less cost effective. The proper treatment of cellulose with phosphoric acid at room temperature causes uniform swelling of the cellulose. As a result, the crystallinity of the cellulose is largely destroyed. At 50°–60° C., the cellulose rapidly hydrolyzes, and consequently, dissolves in the acid to give a viscous solution. The viscosity of the reaction solution decreases as the hydrolysis of the cellulose progresses.

The decrystallization/depolymerization of cellulose can be performed at room temperature, but the depolymerization reaction is very slow and can take several days to produce the desired low crystallinity cellulose product with the desired degree of reduced polymerization. If the reaction between cellulose and phosphoric acid is performed at 50°–60° C., without an initial one hour treatment at room temperature, the product is a highly crystalline product.

The low crystallinity cellulose dissolved in the acid can be suitably separated by combining the reaction mixture under high shear mixing with water or an organic solvent which is miscible with phosphoric acid, but which does not dissolve LCC (e.g., acetone, methanol, and ethanol). Water solvent mixtures may also be used. Filtration, followed by washing the white solid with water to a near neutral pH, provides a hydrated LCC cake. If desired, the neutralization of the acid, associated with the solid, can also be suitably effected by washing initially with an aqueous base such as aqueous alkali metal hydroxide or ammonium hydroxide, followed by water to remove the residual base from the solid. The filtration of the LCC solid can be readily performed using any of the conventional separation techniques, such as vacuum filtration, decantation, and centrifugation.

The aqueous colloidal dispersion of LCC is prepared by suspending and homogenizing the hydrated LCC cake in water. A high-shear mixer or a homogenizer or a household blender can be used. The LCHC dispersions containing 10% or higher weight percentage LCC contents are creams to heavy pastes, whereas those with more than 3% and less than 10% LCC are lotion-like in consistency. The viscosities of the lotion-type dispersions increase with an increase in the LCC content. All dispersions containing less than 3% LCC settle during storage. Such dispersions, however, can be readily stabilized by adding minor, but effective amounts of a water soluble viscosity imparting agent such as, carboxymethylcellulose, methyl cellulose, hydroxypropylcellulose, hydroxypropylmethylcellulose, polyvinylpyrrolidone, cross-linked acrylic acid polymers (Carbopol®Resins), and the like. A water insoluble suspending agent such as bentonite, fumed silicas, modified clays (Thixogel), or the like, can also be used. LCHC also forms stable dispersions in hydroalcoholic mixtures, in water miscible solvents e.g. ethanol, methanol, isopropanol, acetone or a mixed water solvent.

Irrespective of the amount of LCC present, these dispersions form extremely adhesive white films on human skin and hair and on a variety of other surfaces (e.g., glasses, metals, and woods). If desired, minor but effective amounts of an appropriate plasticizer such as glycerin, propylene glycol, mineral oil, citric acid esters, N,N-m-diethyltoluamide, diethyl phthalate, dibutyl sebacate, and the like, can be added to the LCC dispersions. When plasticized, these dispersions form transparent, flexible, non-tacky, and non-oily films.

The aqueous colloidal dispersions of LCC are microbiologically stable at room temperature for many months. It is, however, preferred to add minor but effective amounts of one or more of the commonly used preservatives such as the phenols, benzoates, parabens, quats (quaternium-15) and the like, to increase resistance and inhibition of any microbial growth.

The preparation of LCPC is achieved by dehydrating the LCC cake with an anhydrous organic solvent, such as acetone, methyl alcohol, iso-propanol, n-butanol, and the like, followed by drying at room temperature or at 50°–80° C., preferably at 70°–75° C. During drying, LCPC converts into a loose agglomerate powder, which can be ground to a desired particle size. If desired, the LCPC can also be prepared by freeze drying the wet LCC cake, or by milling spray dried materials.

The LCBC is prepared by spray drying an aqueous colloidal dispersion of LCC. The suitable concentration range of the LCC dispersions, for spray drying, is from about 1% to 8%, preferably about 3–6%. The size of the primary particles of LCBC ranges between 0.2 µm and about 1.0 µm, but most of the particles are about 0.5 µm or smaller. The particle size of the LCBC agglomerate, however, ranges from 5 to 250 µm (FIG. 2), but a typical product may have about 90% or more of its particles in a size smaller than 45 µm. Dispersions containing higher than 8% LCC do not have adequate flow and atomization properties, owing to their highly viscous nature, and are, therefore, not suitable for spray drying.

Figure 2:
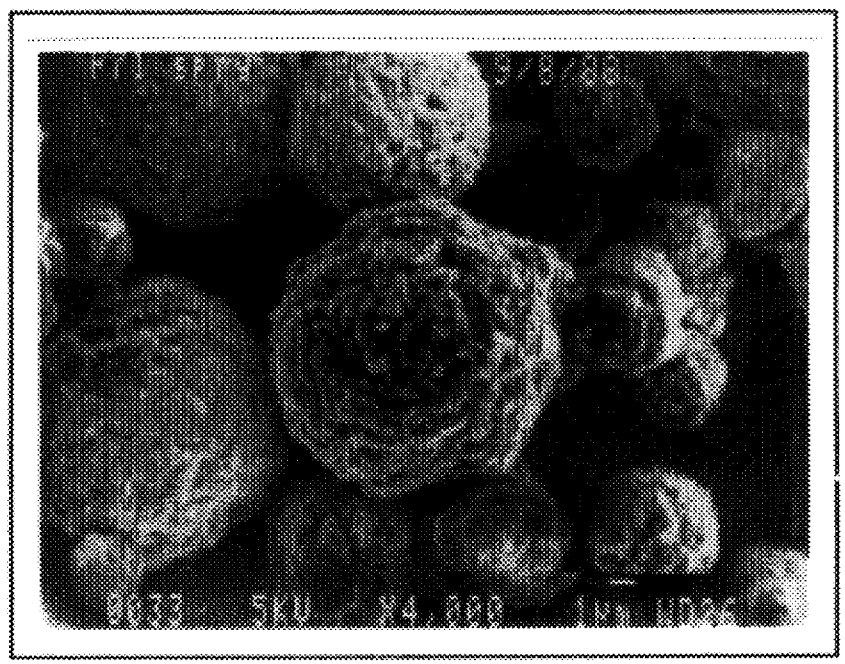
FIG. 2 is a scanning electron micrograph of low-crystallinity bead cellulose (LCBC) of this invention.
Figure 3:
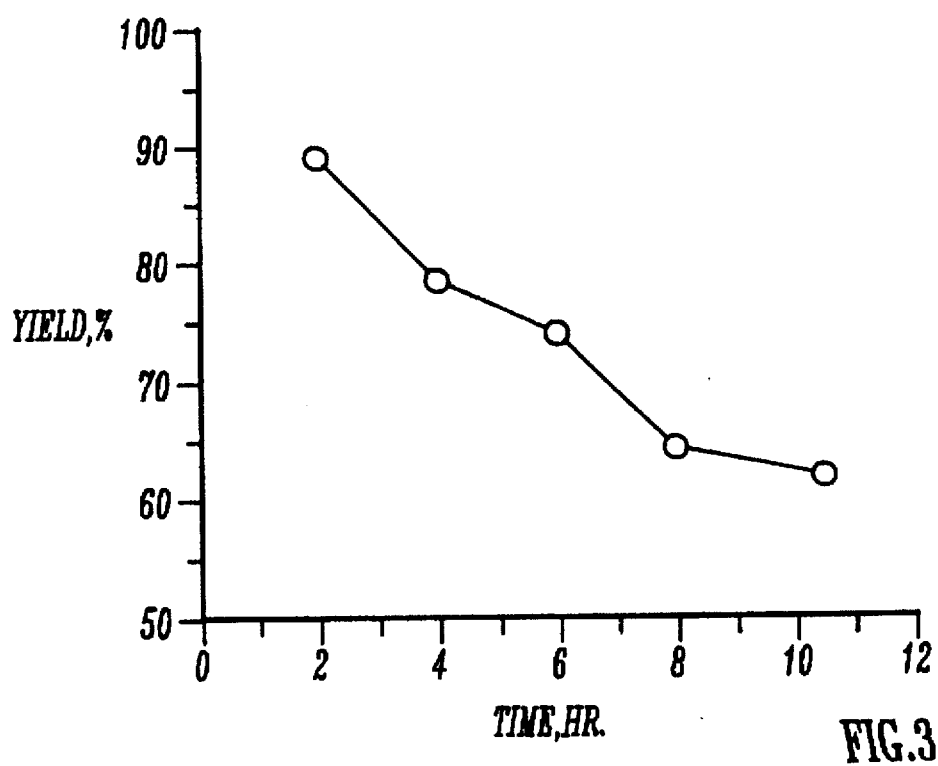
FIG. 3 is a graph showing yield of the low-crystalline cellulose (LCC) product yield in comparison with reaction time at 50° C.

The yield of LCC ranges from 60% to 90%. As shown in FIG. 3, it decreases with an increase in the reaction time at 50°–60° C. A scanning electron micrograph of LCPC, prepared by dehydration of an LCC cake with iso-propanol, followed by drying at 75° C., is shown in FIG. 1, while that of an LCBC is reproduced in FIG. 2. The LCPC appears as an agglomerated powder consisting of primary spherical particles of about 0.5 µm size, whereas the LCBC agglomerates are spherical in shape comprising several primary particles of 0.2 to 0.5 µm size.

Figure 4:
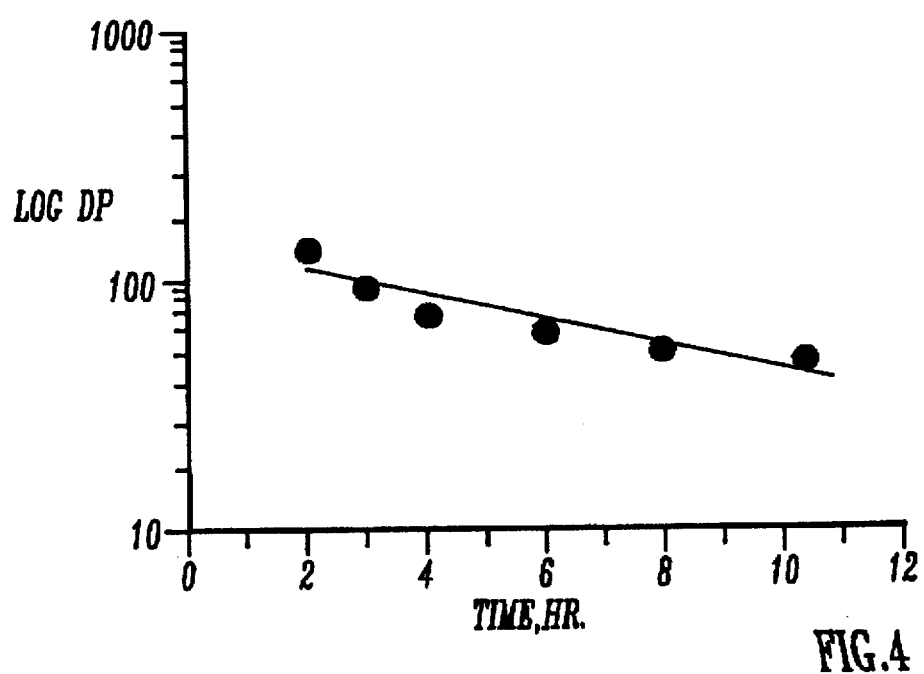
FIG. 4 is a graph showing degree of polymerization of LCC with an increase in reaction time at 50° C.

The degree of polymerization of LCC decreases with an increase in the reaction duration at 50°–60° C., as shown in FIG. 4. It ranges from 35 to 180, preferably 80 to 135. The linear relationship between the reaction time and the logarithm of the degree of polymerization values indicates that the depolymerization of cellulose by phosphoric acid, under the conditions of this invention, is a first-order reaction, with a rate constant value of 0.314 hour$^{-1}$. The first-order rate constant for the depolymerization of cellulose at room temperature is $4.79 \times 10^{-3}$ hour$^{-1}$.

Figure 5:
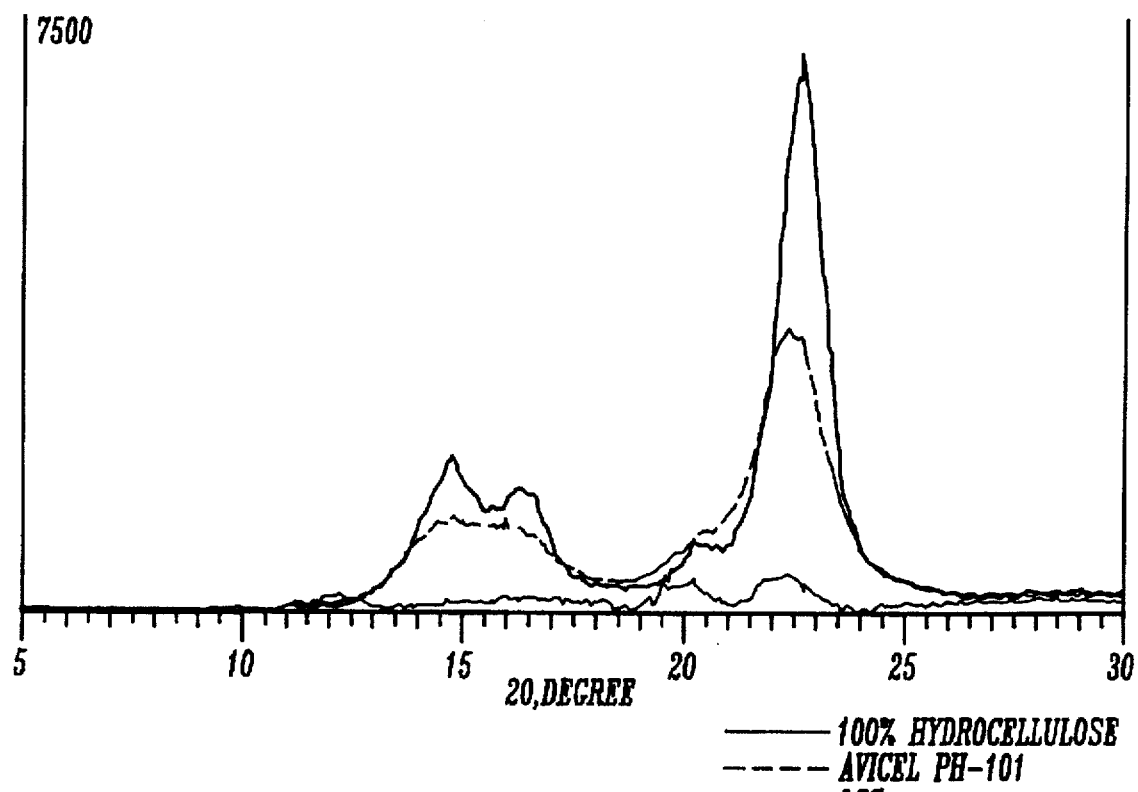
FIG. 5 is an x-ray powder diffraction pattern of LCC and for comparison purposes of a prior art hydroxycellulose product.

The x-ray powder diffraction pattern of LCC is shown in FIG. 5. Also included in the figure are the powder diffractograms of a hydrocellulose product (prepared according to the method provided in U.S. Pat. No. 3,146,170), employed as a 100% crystalline standard, and of Avicel®PH-101. Except for an additional line at 7.4Å, the diffraction pattern of LCC is very similar to those displayed by the Avicel®PH-101 and the hydrocellulose samples. Based on the integration of all diffraction peaks (i.e., the total area under the peaks), the degrees of crystallinity for LCC and Avicet®PH-101 are 15% and 81% respectively.

Figure 6:
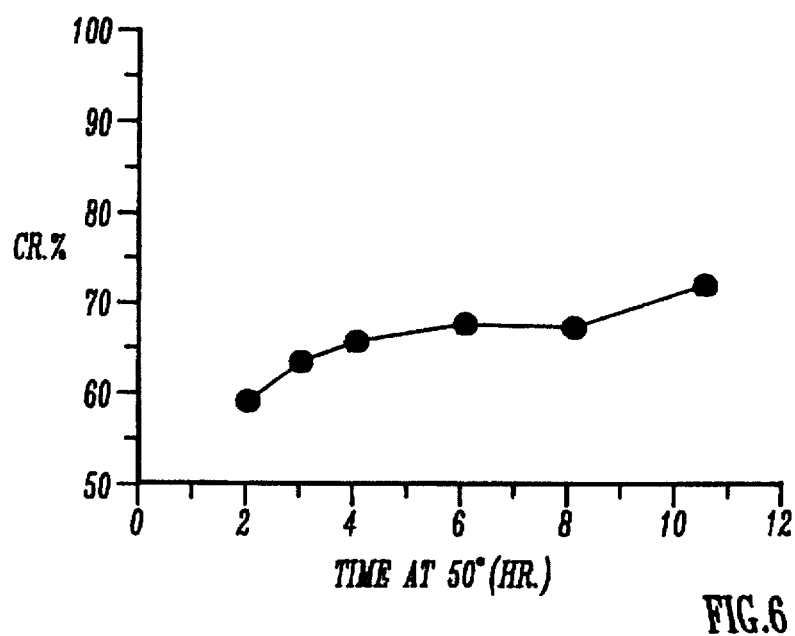
FIG. 6 is a plot showing the crystallinity of LCC increased with an increase in reaction time at 50° C.
Figure 7:
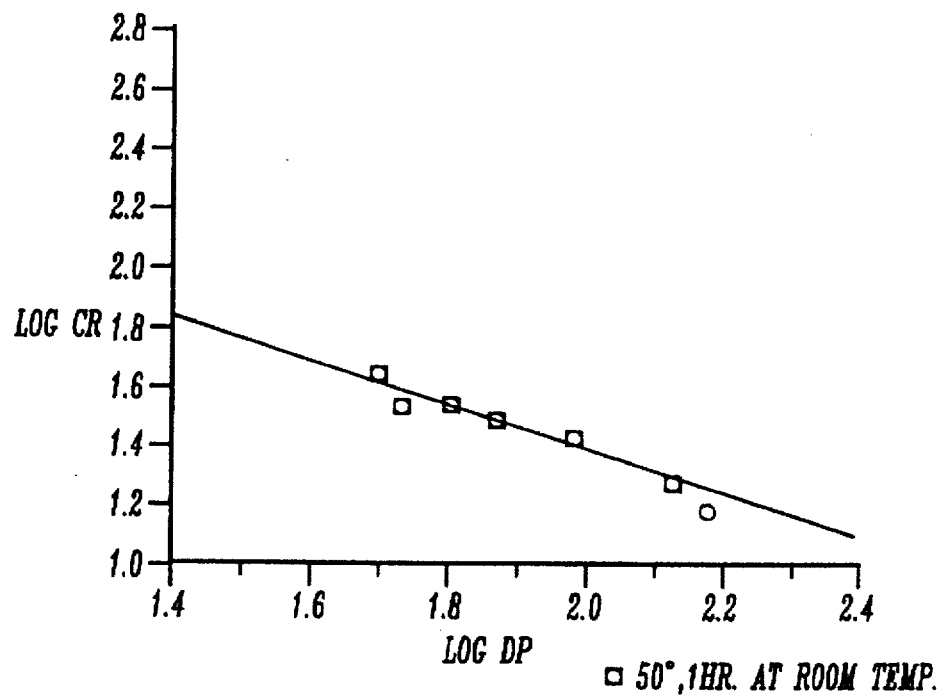
FIG. 7 is a plot showing the inverse relationship between degree of polymerization and LCC crystallinity.

The crystallinity of the LCC increases with an increase in the reaction time at 50°–60° C., as shown in FIG. 6. By way of explanation, and not wishing to be limited thereby, as noted above, the degree of polymerization of the product decreases with an increase in the reaction time. This causes an increase in the particle's surface area. The larger the surface area, the greater the interaction between particles (cellulose chains), and consequently, the higher the crystallinity. This inverse relationship between degree of polymerization and crystallinity of LCC products is shown in FIG. 7. It must be noted that the crystallinity of microcrystalline cellulose increases with an increase in the degree of polymerization. Thus, in this invention, where a simultaneous low degree of polymerization and low degree of crystallinity are sought, very precise control of reaction times and temperatures are required.

Figure 8:
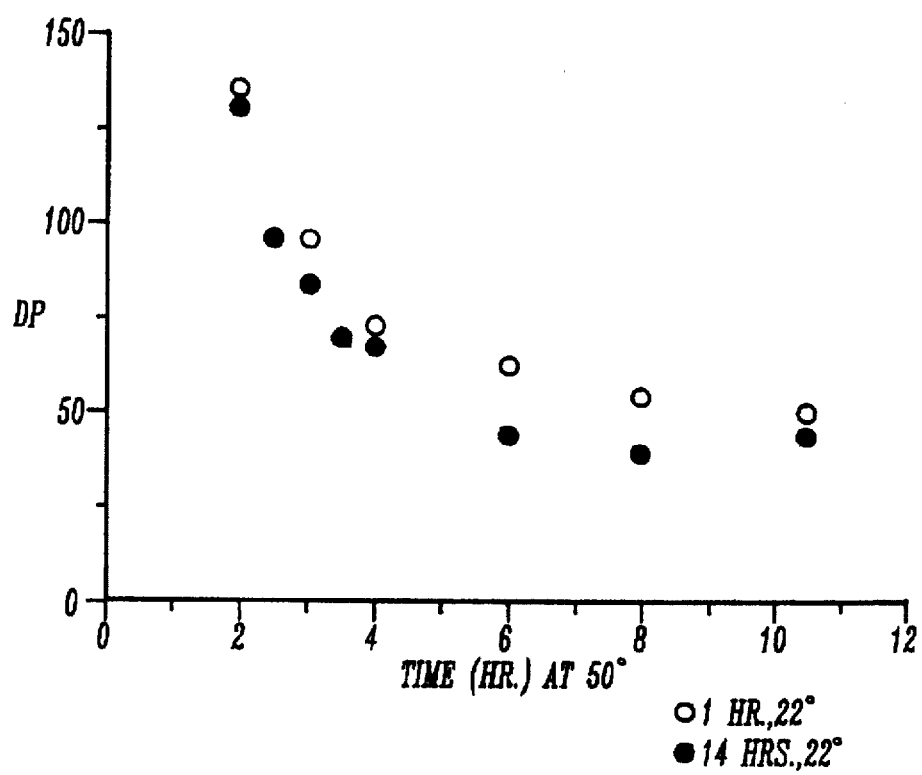
FIGS. 8 and 9 show the effects of swelling time at room temperature on the degree of polymerization of LCC products.
Figure 9:
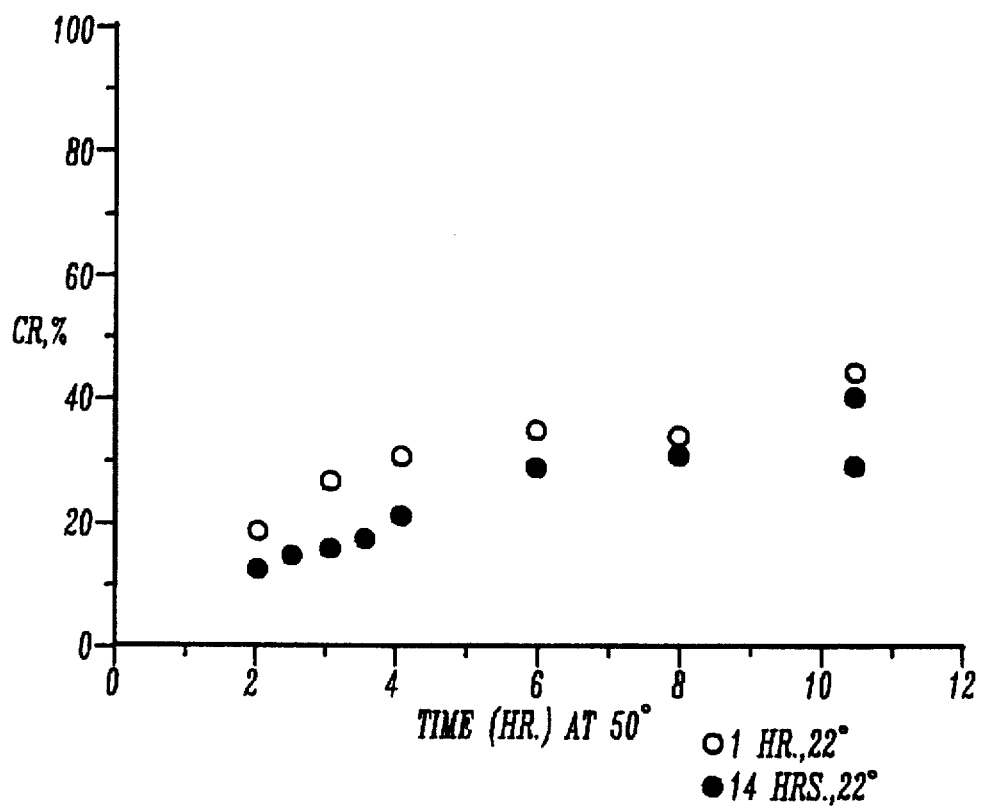

In FIGS. 8 and 9, the effects of swelling time (i.e., duration of acid treatment at room temperature) on the degree of polymerization and crystallinity of LCC products, are compared. The results show no significant changes in the two properties when the reaction duration, at room temperature, is increased from one hour to fourteen hours. These findings, and the fact that the direct treatment of cellulose with phosphoric at 50°–60° C., without an initial treatment at room temperature, produces a highly crystalline product, suggest that an initial swelling period of about one hour or less at room temperature, is critical to the preparation of LCC.

Compared to LCPC, LCBC shows a slightly higher degree of crystallinity. This, probably, occurs due to the recrystallization of LCC, to a small extent, in water, during spray drying.

The mean specific surface areas of LCPC and LCBC particles are 2.45 m$^2$/g and 2.33 m$^2$/g, respectively. The small difference in specific area between the powder and bead materials confirms that the primary particles comprising the beads are loosely associated, and hence lose little of their effective surface area. LCBC shows a higher bulk density and lower porosity compared to LCPC. The bulk densities for the LCBC and LCPC are 0.85 g/cm$^3$ and 0.431 g/cm$^3$, and the porosity values are 49.1% and 72.7%, respectively. This difference in the bulk densities and porosities of the two products are due to the differences in the particle's shapes. The LCBC particles, as shown in FIG. 2, are highly spherical in shape, which facilitates a more tightly packed powder bed, whereas LCPC is a highly agglomerated powder composed of irregular-shape particles, which, when packed, has more void spaces as a result of entanglement or interlocking of particles. The densities and porosities of the LCPC and LCBC compacts, prepared by compressing 0.5 grams of the LCPC and LCBC each at 3000 lb for 30 seconds, are 1.381 g/cm$^3$ and 1.241 g/cm$^3$ and 21.4% and 12.6%, respectively. The density values suggest a larger volume reduction for the LCPC compact than for the LCBC compact. This occurs because the LCBC particles retain their integrity, to a large extent, under compression, whereas the LCPC particles undergo significant plastic flow, thereby filling void spaces and forming new bonds on the true contact areas.

Figure 10:
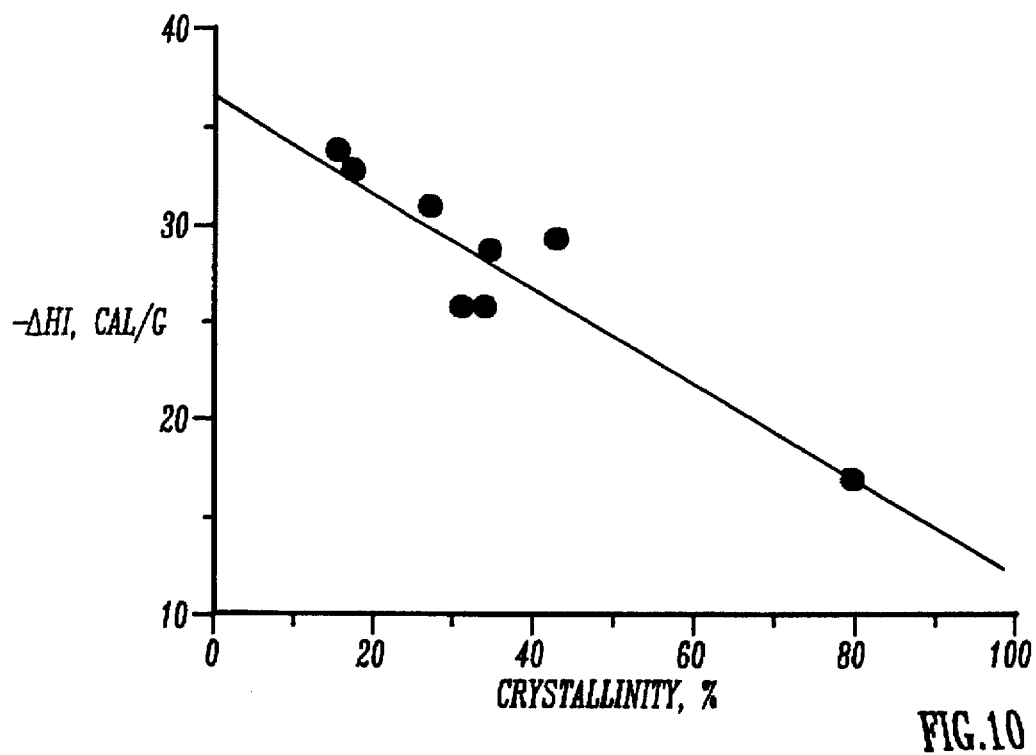
FIG. 10 compares the heat of immersion of LCC product and a conventional product.

Calorimetric methods have been widely used to study the heat of wetting or other properties of water insoluble excipients such as interactions between additives. Calorimetry measures a progressing change of an extensive property, enthalpy, as one physical state is changing to another state. The enthalpy of immersion, ($\Delta H_i$), is the heat of immersion of the solid, representing energy changes due to wetting, hydration, swelling, surface changes, or the release of stored energy of solids in water. Thus, cellulose excipients having different levels of crystallinity would be expected to show different enthalpies of immersion. FIG. 10 compares the heat of immersion of various LCC products, provided by this invention, and Avicel®PH-101 having a percent of crystallinity of 80%. The negative $\Delta H_i$ values obtained indicate that the interaction between cellulose and water is an exothermic reaction. The $-\Delta H_i$ increases with a decrease in the crystallinity of the cellulose. This is because as the crystallinity decreases more hydroxyl groups become available for interactions with water, and consequently, the $\Delta H_i$ increases. The $\Delta H_i$ values for the LCPC and LCBC products, having 27% crystallinity, are $-31.01$ cal/g and $-19.66$ cal/g, respectively, whereas the corresponding value for the Avicel®PH-101 is $-16.74$ cal/g. When LCBC is compressed at a pressure of 3000 lb for 30 seconds, the $\Delta H_i$ is increased by 9.8%. This increase in the $\Delta H_i$ value on compression is due to the increased defect structure, and release of elastic energy stored in the LCBC compact as a result of compression. The $\Delta H_i$ of the LCC is also dependent on the moisture content present, increasing with a decrease in the moisture amount. For example, the $\Delta H_i$ values for LCPC containing 5% and 0% moisture are 24.72±0.53% cal/g and 31.02±1.92 cal/g, respectively.

Figure 11:
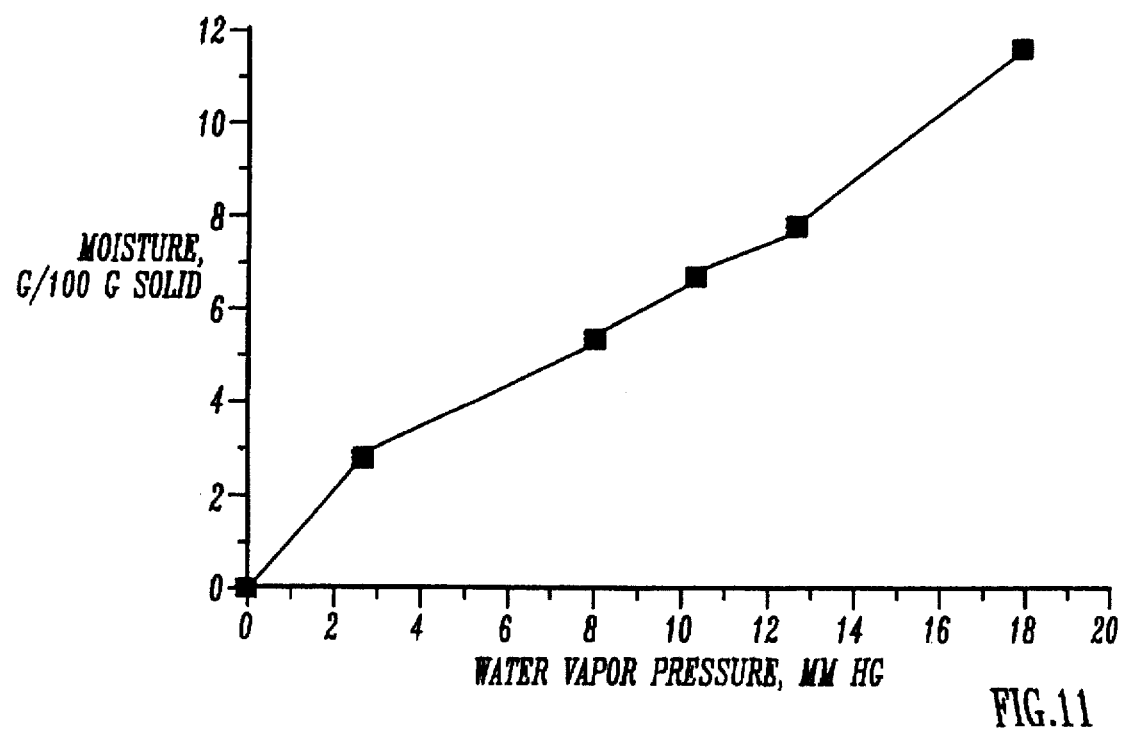
FIG. 11 shows the moisture sorption isotherm of low crystalline powdered cellulose (LCPC) against water vapor pressure.

The heat of wetting, $\Delta H_w$, of LCC, calculated from $\Delta H_i$ using Hess's Law, is $-6.9$ cal/g, about 27.1% higher than that reported for Avicel®PH-101 (R. G. Hollenbeck, G. E. Peck, and D. O. Kildsig, *J. Pharm. Sci.*, 67, 1599 (1978)). The moisture sorption isotherm of LCPC against water vapor pressure is shown in FIG. 11. The moisture content increases with an increase in the water vapor pressure.

The preparations of LCC, LCPC, LCBC, and LCHC and their applications in the formulation of a variety of pharmaceutical, cosmetic, and personal care products are illustrated by the following examples, which are not to be construed as limiting.

EXAMPLE 1

Decrystallization/depolymerization of Cellulose Using Phosphoric Acid

One thousand milliliters of 85–86% phosphoric acid was placed in an appropriate size flat-bottom glass or polyvinylidine fluoride container. To this was added 100 grams of cotton linter sheet, broken into small pieces, or cotton linter fluff. The thoroughly wetted cellulosephosphoric mixture was then allowed to stand at room temperature for about one hour. The reaction container was then placed in a water-bath that had been adjusted to 50°–60° C. After about one and one half to two hours of heating, the reaction mixture was stirred using a mechanical stirrer equipped with an acid-resistant propeller and a shaft. Mixing and heating were continued until a light cream colored solution was formed (about 2–3 hours). The reaction solution was immediately poured into water with vigorous stirring. The water volume can be about five-to-ten times that of the acid volume. An immediate precipitation of white solid occurred. The solid was then filtered using a buchner funnel and a Whatman Grade-113 filter paper. An extensive washing of the solid with water followed, to a near neutral pH of the wash water, to produce a hydrated low crystallinity cellulose (LCHC), with an 85–90% yield (based on the dried weight basis). [If desired, the white solid residue can be washed first with an aqueous solution of a base, such as sodium or potassium hydroxide or ammonium hydroxide, and then with water to remove the inorganic phosphates.]

EXAMPLE 2

Preparation of Low Crystallinity Powder Cellulose (LCPC)

The hydrated white cake, prepared according to the procedure of Example 1, was dispersed in an appropriate volume of methanol, ethanol, acetone, or iso-propanol. The mixture was stirred with a mechanical stirrer for about 15 minutes, or until a uniform dispersion was formed and then filtered. This process was repeated three-to-five times to ensure complete depletion of water from the cellulose. The dehydrated low crystallinity cellulose residue was then broken into small lumps with a spatula, and dried either at room temperature overnight or at 75° C. for 4–6 hours. Following drying, the low crystallinity cellulose powder was ground with a mortar and pestle or using a pulverizing blender, to reduce the particle size of the agglomerates to below 125 μm.

EXAMPLE 3

Preparation of Low Crystallinity Bead Cellulose (LCBC)

The low crystallinity hydrated cellulose, prepared according to the procedure of Example 1, was homogenized in an appropriate amount of distilled purified water, to give an LCC concentration of about 4–8%. The resulting homogeneous colloidal dispersion was then spray dried, using a Nitro Utility Spray Dryer (Nitro Atomizer, Ltd., Columbia, Md., USA), equipped with a 12 cm diameter radial vane centrifugal atomizer, operating at 24,000 rpm and an inlet temperature of about 200±5, and an outlet temperature of 100±3. The low crystallinity bead cellulose powder, thus obtained, was collected, and passed through a #120(125 mm) sieve.

EXAMPLE 4

Figure 12:
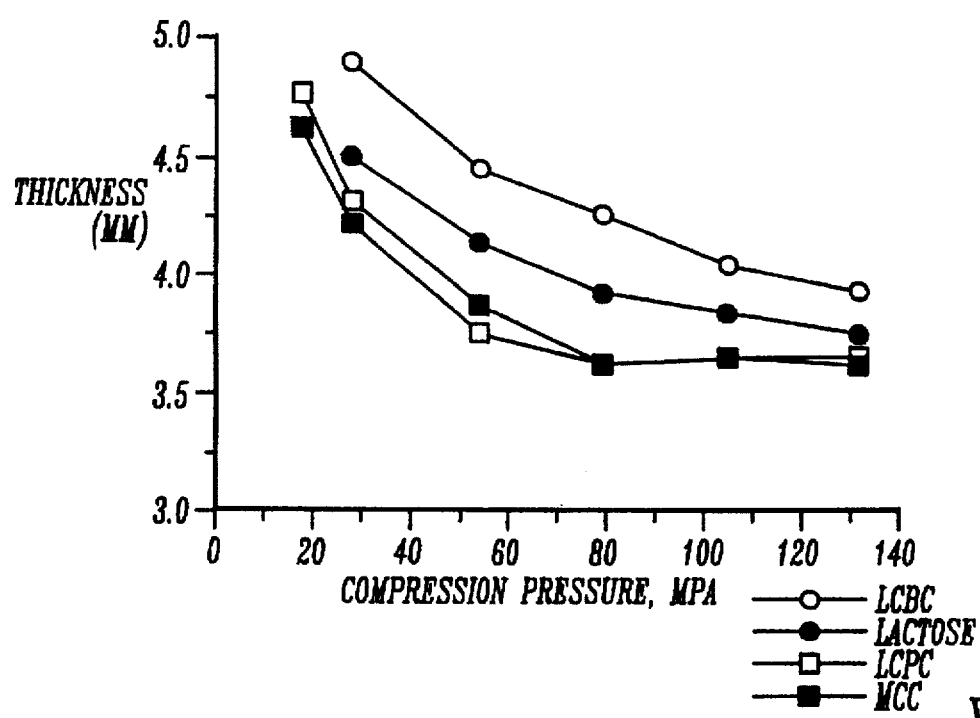
FIG. 12 shows the thickness of tablets prepared at different compression pressures for tablets using LCBC of this invention and other materials showing LCBC tablets show the least reduction.
Figure 13A:
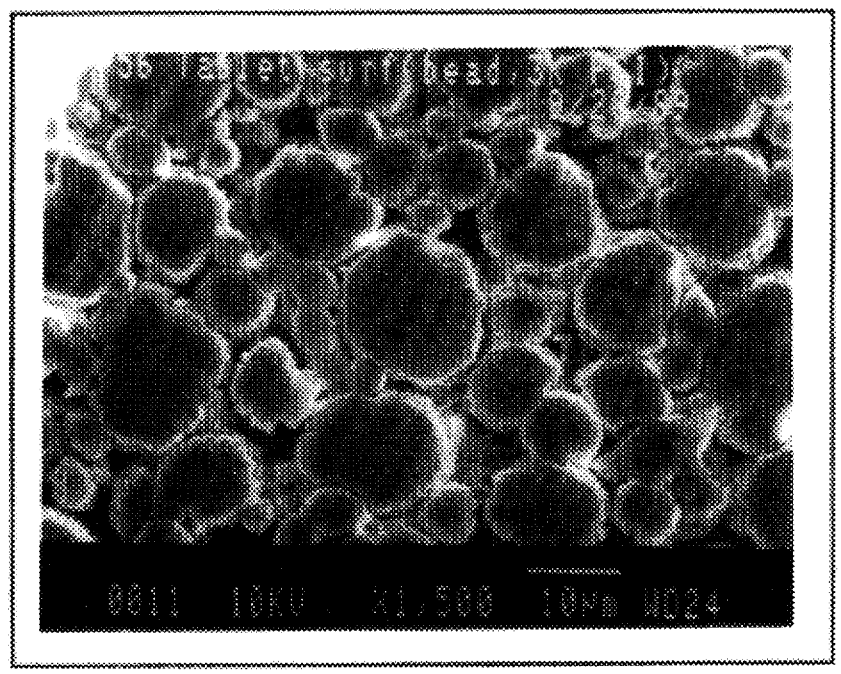
FIG. 13 shows a scanning electron micrograph of the LCBC tablet with 13(a) showing the surface and 13(b) a cross section of the tablet.
Figure 13B:
Figure 14:
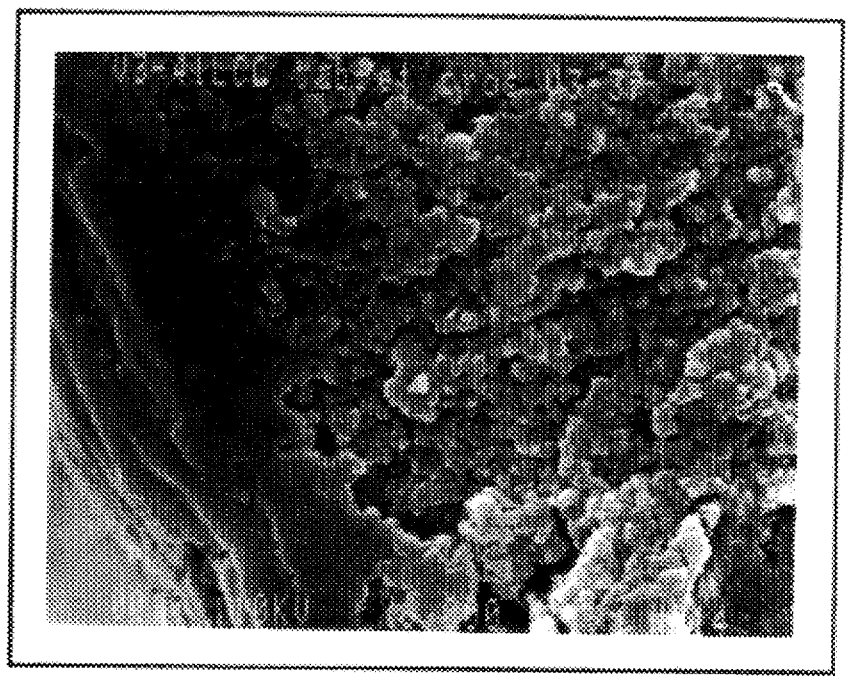
FIGS. 14, 15A and 15B show comparisons scanning electron micrographs of LCPC and Avicel®PH-101 tablets for comparison with FIG. 13.
Figure 15A:
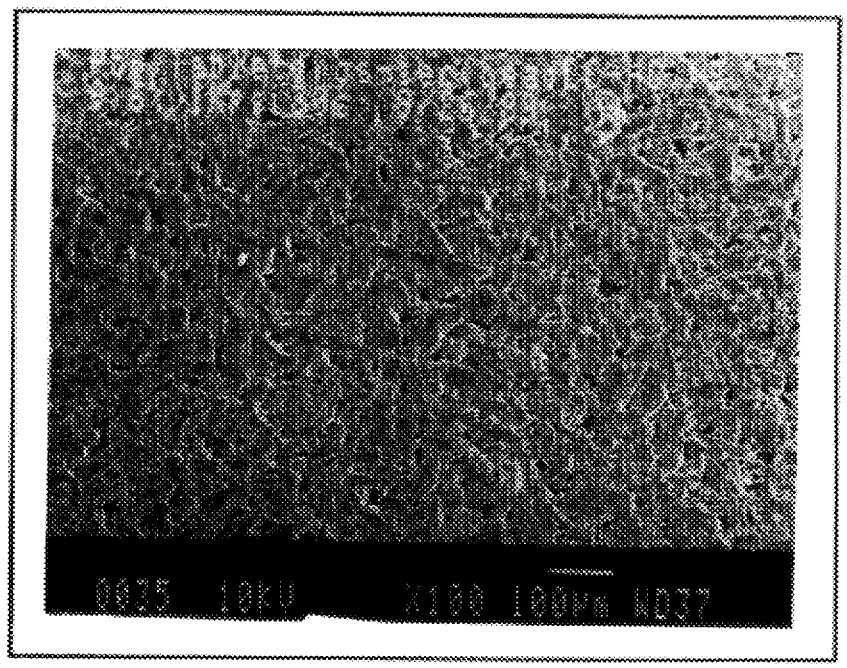
Figure 15B:
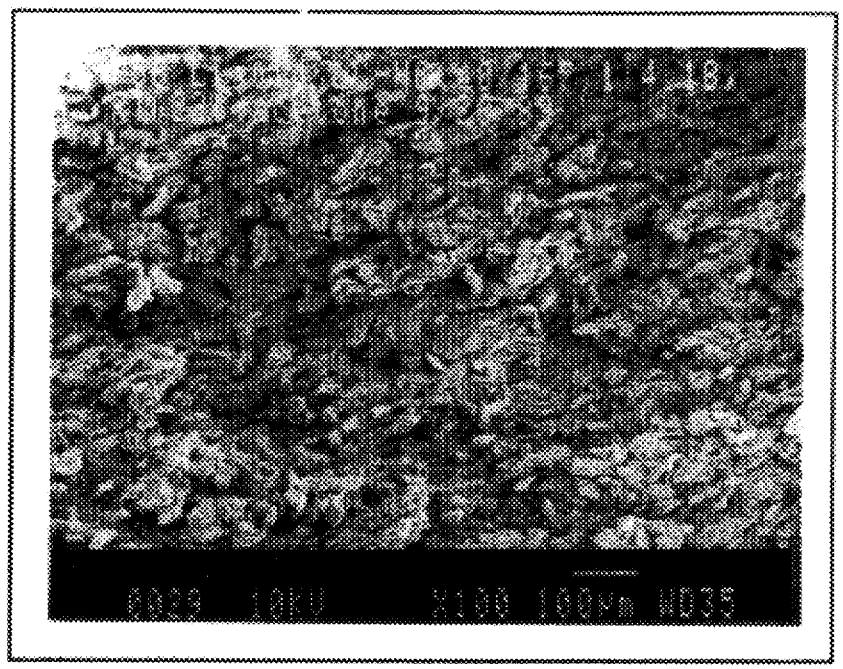

Comparative Evaluation of LCPC and LCBC as Direct Compression Excipients in Tablets A. As Binders 0.5 grams of LCPC and LCBC, prepared according to the procedures of Examples 1–3, were separately compressed for 20 seconds, without a lubricant, into cylindrical flat-face tablets at different compression loads using the same punch (flat-faced) and die (11 mm diameter). Tablets of Avicel®PH-101 and lactose, employed for comparison purposes, were also prepared in the same manner. The results obtained are discussed below:

The thickness of the tablets prepared at different compression pressures is depicted in FIG. 12. LCBC tablets show the least volume reduction, whereas Avicel®PH-101 and LCPC tablets exhibit the highest. The lactose tablets show smaller volume reduction, compared to the LCPC tablets (and Avicel®PH-101), but higher than for the LCBC tablets. The low compressibility of the LCBC material is attributed to its inability to undergo plastic flow, under compression. This is reflected in the scanning electron micrograph (of the LCBC tablet) depicted in FIG. 13, which shows a deformed compressed bead structure (FIG. 13b), with large void spaces (FIG. 13a), and definite boundaries between the particles. In comparison, the scanning electron micrographs of LCPC and Avicel®PH-101 tablets (FIGS. 14 and 15) demonstrate strong interactions between the primary particles, with disappearance of some boundaries, especially in regions near the edges of the tablet. This accounts for the higher compressibility of these materials. The smaller thickness of the lactose tablets, compared to the LCBC tablets, is due to the fragmentation of the lactose particles, under compression, which fill the interparticle spaces to produce a relatively tightly packed compact.

Figure 16:
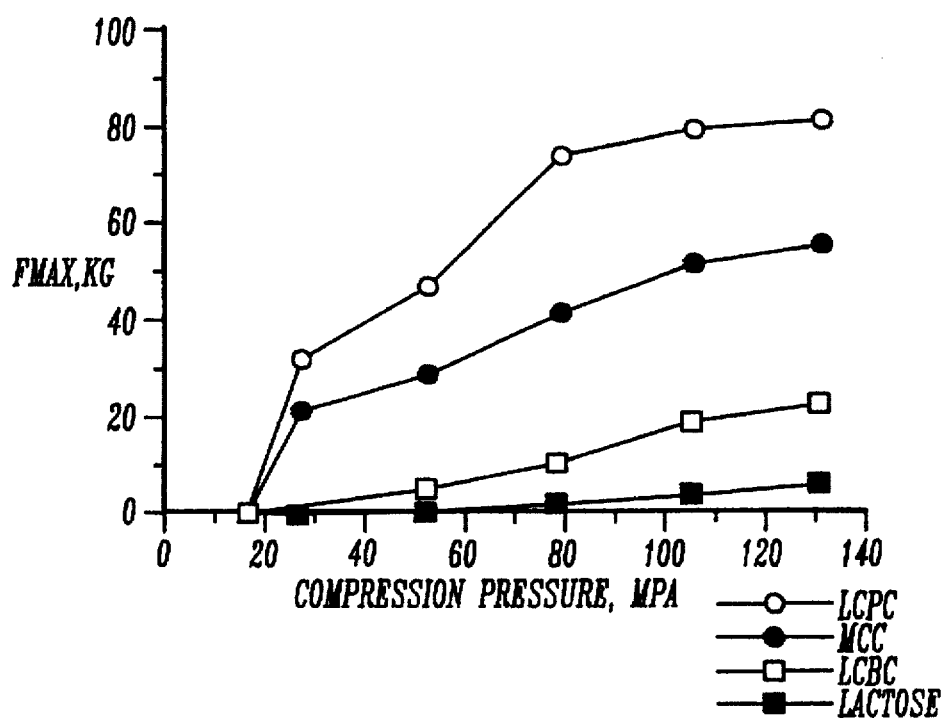
FIG. 16 compares crushing strengths of LCPC, LCBC, Avicel®PH-101 and lactose tablets, indicating superior binding properties of LCPC.
Figure 17:
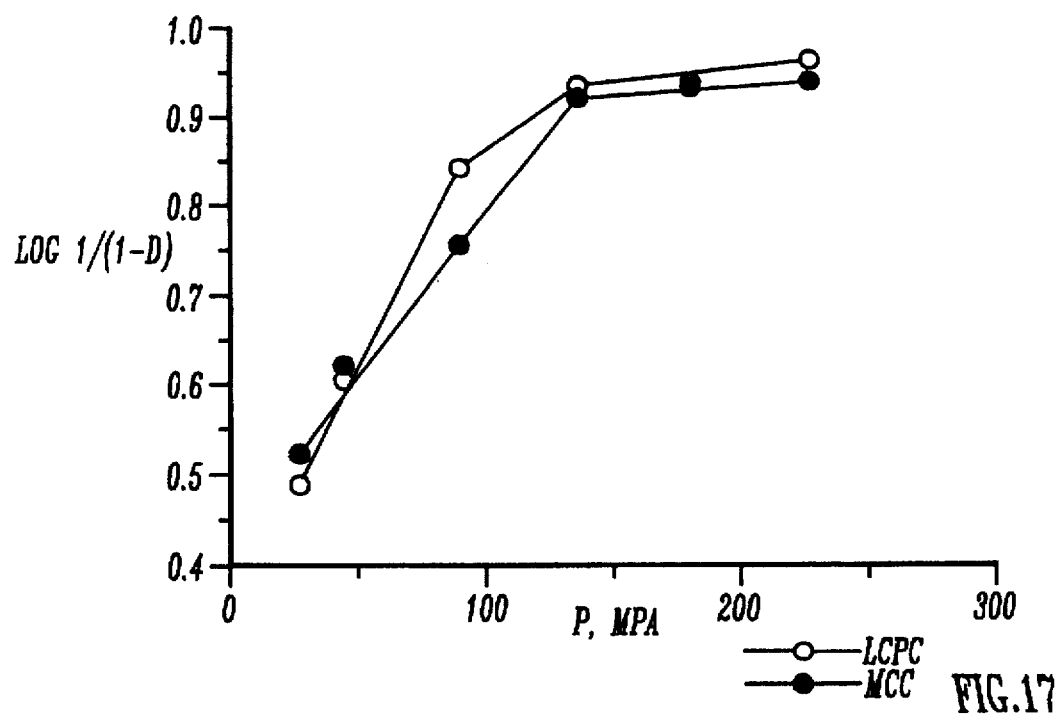
FIG. 17 shows Heckel plot analysis of LCPC compared to Avicel®PH-101, again demonstrating superior binding properties of LCPC.

FIG. 16 compares the crushing strengths of LCPC, LCBC, Avicel®PH-101, and lactose tablets. The highest crushing strength values for the LCPC tablets clearly indicate superior binding properties of the LCPC material. The poorer compatibility (i.e. binding properties) of the Avicel®PH-101, compared to LCPC, is due to its higher crystallinity. This is because as the crystallinity increases, a smaller number of hydroxyl groups become available for interactions. As a result, the weaker tablet is formed. Further support for the superior binding properties of the LCPC material, compared to Avicel®PH-101, is provided by Heckel Plot analysis (FIG. 17). The linear portions of the plots indicate that both LCPC and Avicel®PH-101 undergo plastic flow under compression. The mean yield pressure values, calculated from the slopes of the linear portions of the curves, are 82 MPa and 125 MPa for the LCPC and Avicel®PH-101, respectively. The lower (mean yield pressure) value for the LCPC indicates that the LCPC material has a greater ability to deform plastically at lower pressure than Avicel®PH-101. Further, LCPC, owing to the agglomeration of primary particles, probably deforms along many planes, whereas Avicel undergoes plastic deformation along slip planes only (R. F. Shangraw, in "Pharmaceutical Dosage Forms: Tablets," H. A. Lieberman, L. Lachman, and J. B. Schwartz, eds., Marcel Dekker, Inc., New York, 2nd ed., Vol. 1, p. 195–96, 209–216 (1989)). These factors make LCPC more compressible than Avicel®PH-101. The porosities of the LCPC and Avicel®PH-101 compacts correspond to 12.5% and 15.4%, respectively, further documenting the tighter packing of the LCPC than Avicel®PH-101 under compression.

LCBC tablets are stronger than lactose tablets. This is because LCBC, owing to its low crystallinity and submicron particle size, demonstrates more extensive hydrogen bonding. In comparison, lactose forms bonds only in the glassy region which constitutes a very small portion of the lactose crystals.

The results of viscoelastic analysis, which provides the energy change in the unloading phase of the tabletting process, including the work due to the elastic deformation and viscous deformation, are presented in Table 1.

TABLE 1

| Cellulose form | LCBC | LCPC | AVICEL PH-101 |
| --- | --- | --- | --- |
| Avg. Wt. | 0.538 | 0.543 | 0.535 |
| P(MPa) | 153 | 173 | 109 |
| $W_o(J/cm^3)$ | −12.30 | −13.04 | −5.23 |
| $W_i(J/cm^3)_a$ | 9.55 | 9.00 | 3.75 |
| $W_{Pdx}(J/cm^3)$ | −2.73 | −3.31 | −1.45 |
| $W_L(J/cm^3)$ | 30.52 | 38.92 | 29.62 |
| Increment | 7 | 8 | 5 |

The stress P values decease in the order from LCPC to LCBC and to AVICEL PH-101. Both LCPC and LCBC show higher negative values for the work due to elastic deformation than AVICEL PH-101. This is due to the submicron particle size of the LCPC and LCBC which provides larger surface area for interactions, and consequently, requires more work for the elastic deformation. AVICEL PH-101 shows extensive interlocking of the fibers, and thereby demonstrates a lower value of the work of elastic deformation. The higher $W_i$ values for the LCPC and LCBC, compared to AVICEL PH-101, suggest that the LCC primary particles undergo a greater extent of viscous flow in the unloading phase of the tabletting process. This results in an increase in the contact area, which facilitates stronger interactions to consolidate the tablet while dissipating the excess energy in the forms of heat and entropy. The higher negative force displacement work values for the LCPC and LCBC, compared to AVICEL PH-101, are due the absence of any interlocking of primary particles in the LCPC and LCBC aggregates. There is no difference in the loading work among the LCPC, LCBC, and AVICEL PH-101. The incremental values, which reflect the extent of expansion in the unloading phase, are consistent with the work values due to elastic deformation. The viscoelastic analysis further documents the superiority of LCPC and LCBC materials as to tablet excipients, compared to microcrystalline cellulose.

Figure 18:
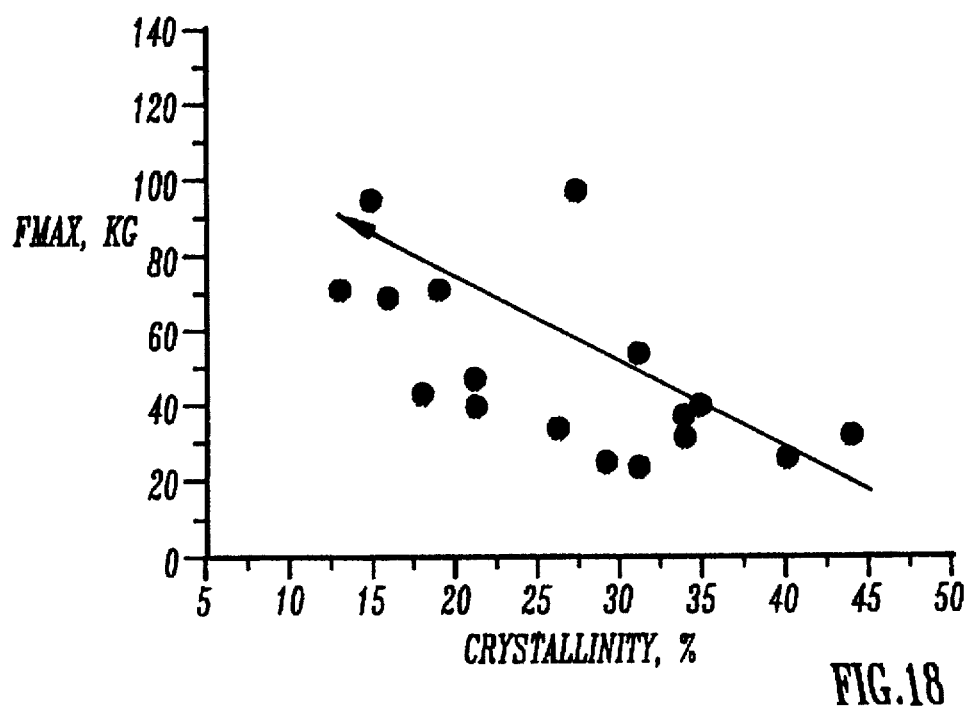
FIGS. 18 and 19 show the effect of crystallinity and degree of polymerization on the crushing strengths.
Figure 19:
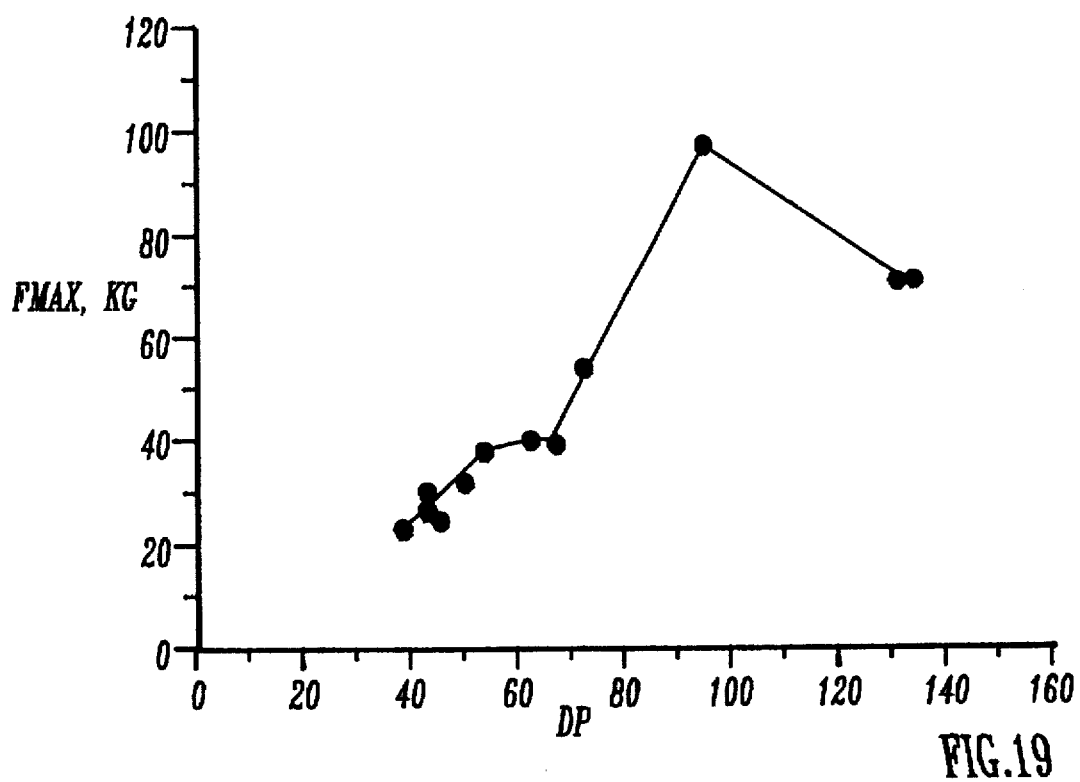
Figure 20:
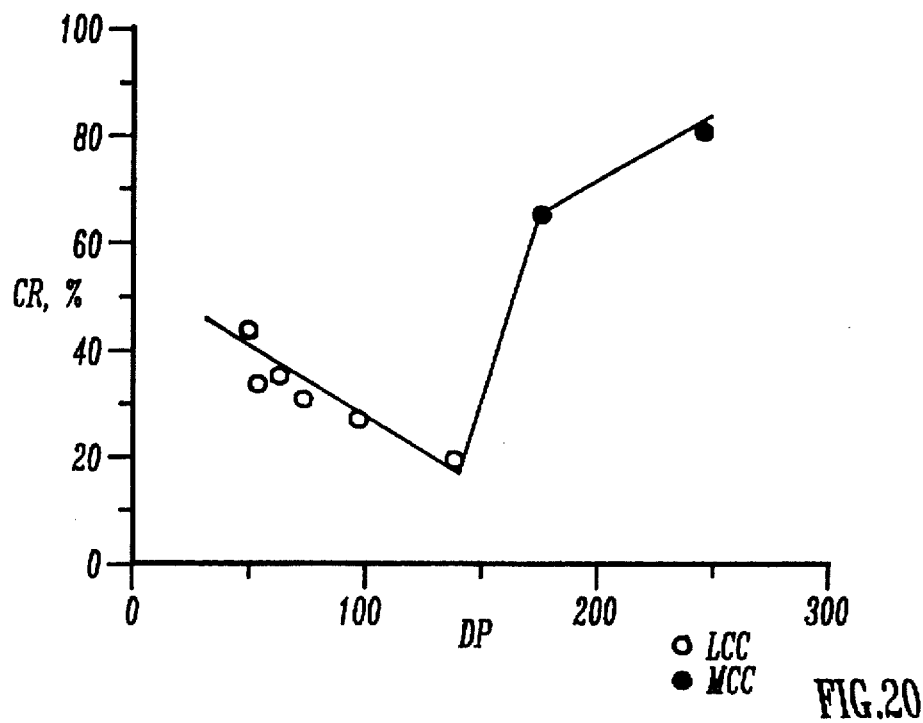
FIG. 20 shows that as the degree of polymerization increases the crystallinity of LCPC first decreases and then increases.

The effects of crystallinity and degree of polymerization on the crushing strengths of the LCPC tablets are depicted in FIGS. 18 and 19. Tablets for this study were prepared by compressing 0.5 grams of LCPC, having different crystallinity and degree of polymerization values, at 3000 lb for 20 seconds. As shown in FIG. 18, the crushing strengths of the tablets increased from 20 Kg to 100 Kg when the crystallinity of the LCC decreased from 45% to 12%. This shows that as the crystallinity decreases, stronger tablets are formed, as would be expected. FIG. 19 shows that the crushing strength of the LCPC tablet first increases then decreases with an increase in the degree of polymerization. This is because as the degree of polymerization increases the crystallinity of LCPC first decreases and then increases, as shown in FIG. 20.

The effect of the particle size on the fluidity of the LCPC compared to a like particle size AVICEL PH-101 powder and on the crushing strength is compared in Table 2.

TABLE 2

| Cellulose form | Particle size (μm) | Flow rate g/sec | Crushing Strength Kg |
| --- | --- | --- | --- |
| LCPC | 50 | 1.75 ± 0.31 | 74.8 ± 2.9 |
| LCPC | 125–350 | 5.61 ± 0.91 | 76.2 ± 1.4 |
| AVICEL PH-101 | 50 | 1.30 ± 0.34 | 58.4 ± 1.8 |

Generally, the larger the particle size of a powder, the better the fluidity or powder flow. However, the crushing strength of plastic materials has been shown to decrease with an increase in particle size (M. Sheik-Salem and J. T. Fell, *Acta Pharm. Suec.*, 19, 391 (1982); A. H. DeBoer et al., *Pharm. Weekblad, Sci. Ed.*, 8, 145 (1986); N. R. Anderson, G. S. Banker, and G. E. Peck, *J. Pharm. Sci.*, 71, 7 (1982)). Thus, the loss of crushing strength, accompanying an increase of particle size, is of general concern in tablet making although larger particles characteristically provide much better powder flow. The data listed in Table 2 indicate that LCPC, irrespective of particle size and flow rate, provide tablets with nearly the same crushing strength values. The significance of this unique property of LCPC is that the preparation of LCPC with a larger particle size, that demonstrates excellent powder flow, at the same time, produces compacts with the same strong cohesion properties as the fine particles. Both adequate powder flow and strong compact cohesion properties are desirable features in excipients used in tablet production. The reason that LCPC possesses this unique property, among tablet excipients, is that the LCPC particles are actually agglomerates, each made up of hundreds to thousands of individual colloidal particles.

B. As Disintegrants

Tablets of LCPC, LCBC, and AVICEL PH-101, each weighing 0.5 grams, were prepared using a Carver press at either 1000 lb for 20 seconds or at 3000 lb for 30 seconds. The heats of immersion, water penetration rate and the disintegration time of the tablets are presented in Table 3.

TABLE 3

| Sample | Water Penetration Rate (mg/sec) | Disintegration Time | Heat of Immersion $\Delta^H_i$ |
| --- | --- | --- | --- |
| LCBC | 3.347 | 5.0 seconds | −21.59 |
| LCPC | 0.0 | — | not detd. |
| AVICEL PH-101 | 1.724 | >1 hour | −13.63 |

Figure 21:
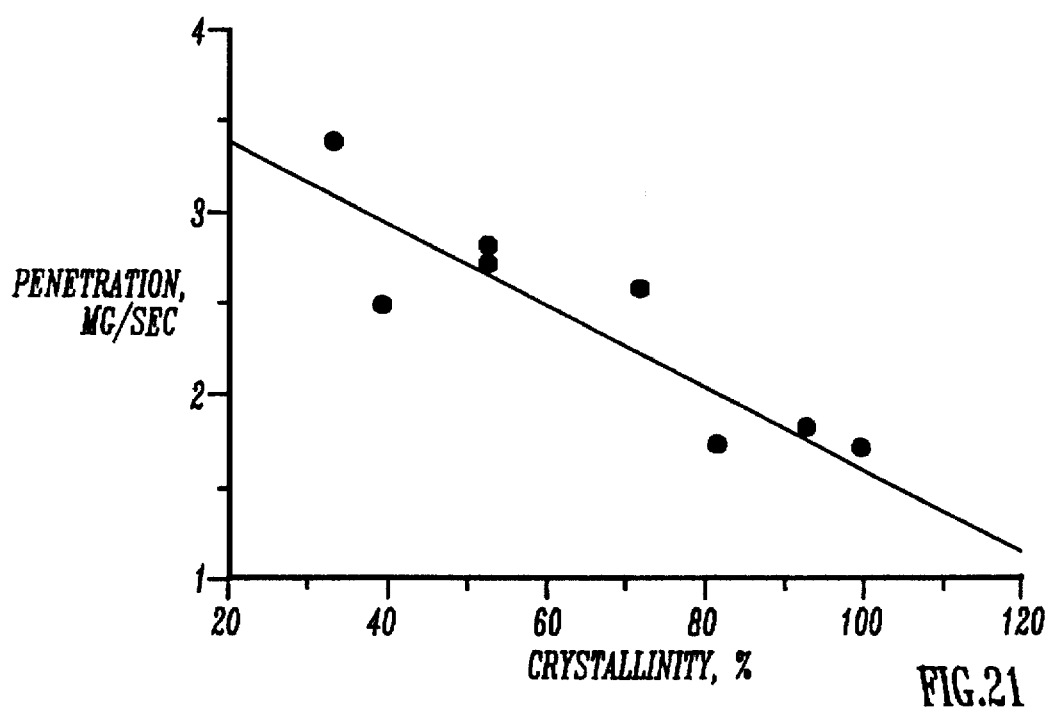
FIG. 21 shows the effect of the degree of crystallinity on the water penetration rate.

The water penetration data show that water penetrates much more rapidly in the LCBC tablets than in AVICEL PH-101 tablets. The LCPC tablets did not show any appreciable penetration of water. The greater water penetration rate of the LCBC tablets is due to its capillary structure (FIGS. 2 and 12) and reduced degree of crystallinity. LCPC, though also having a reduced degree of crystallinity, undergoes high plastic flow under compression, causing the primary particles to pack themselves very tightly (see FIG. 14). The penetration of water in the AVICEL tablet occurs through the void spaces produced as a result of entanglement or interlocking of primary particles during compression (see FIG. 15):

The effect of the degree of crystallinity on the water penetration rate is depicted in FIG. 21. As is evident from the Figure, the water penetration increases with a decrease in the crystallinity, because more and more free hydroxyl groups become available for interactions.

The rapid disintegration of the LCBC tablet compared to the AVICEL PH-101 tablet is due to its greater capillary action. Other factors that contribute to its superior disintegrating properties include the lack of entanglement of primary particles, release of stored mechanical (elastic) energy as the tablet disintegrates, stronger affinity for interaction with water, and the release of a higher heat of immersion.

EXAMPLE 5

Comparative Evaluation of LCPC and AVICEL PH-101 as Binders in Acetaminophen Tablets Test tablets were prepared by thoroughly mixing 320 mg of acetaminophen, a poorly compressible material, with 175 mg of LCPC or AVICEL PH-101, and 5 mg of magnesium stearate, followed by compression at a pressure of 3000 lb for 20 seconds using a Carver press. A commercial acetaminophen tablet, Tylenol®, having the same tablet size and drug content, was also tested for comparison. The results are presented in Table 4.

TABLE 4

| Tablet Type | Disintegration Time (min) | Crushing Strength (Kg) |
| --- | --- | --- |
| LCPC | 11.4 ± 0.2 | 9.00 ± 1.14 |
| AVICEL PH-101 | 14.6 ± 2.1 | 6.53 ± 0.40 |
| Tylenol | 0.68 ± 0.03 | 8.70 ± 0.03 |

The higher crushing strength of the LCPC-acetaminophen tablets compared to the AVICEL PH-101 tablets is consistent with the superior cohesion properties of the LCPC. The LCPC-acetaminophen also disintegrates faster than the AVICEL tablet (11.4 min. vs. 14.6 min.). This is due to the stronger affinity of the LCC material with water. Compared to LCPC and AVICEL-acetaminophen tablets, the Tylenol® tablet disintegrates very rapidly, and shows an intermediate crushing strength value.

The strong cohesion properties of the LCPC, coupled with its excellent flow properties and effectiveness as a disintegrant in drug mixture systems, demonstrate the unique usefulness and superiority of LCPC as a direct compression combined binder/disintegrant/diluent excipient material in tablet making.

EXAMPLE 6

Disintegration of LCBC-Griseofulvin Tablets

LCBC-Griseofulvin tablets, comprised of 215 grams of LCBC and 250 grams of griseofulvin, were prepared in the same manner as described in Example 6. The disintegration time and the crushing strength values of the tablets are listed in Table 5. Fulvicin U/F, a commercial griseofulvin tablet containing the same amount of drug and of the same size as the test tablet, was employed as a reference.

TABLE 5

| Tablet Type | Disintegration Time (min) | Crushing Strength (Kg) |
| --- | --- | --- |
| LCBC | 0.88 ± 0.15 | 23.8 ± 0.61 |
| Fulvicin U/F | 1.48 ± 0.18 | 11.6 ± 0.93 |

The LCBC-griseofulvin tablet demonstrated a faster disintegration time (0.88 minutes versus 1.48 minutes) and a stronger crushing strength (23.8 Kg versus 11.6 Kg) than the commercial griseofulvin tablet.

EXAMPLE 7

Preparation of Cream, Lotion and Spray Formulations Using LCHC

Owing to its high suspendibility in water and hydroalcoholic solvent systems and its ability to form extremely adhesive films on the skin, LCHC can be used to prepare a wide range of pharmaceutical (topical and transdermal), cosmetic, agricultural, and like products. Conventional formulation procedures can be used to prepare cream, lotion, and spray products, utilizing the present LCHC material. For example, various formulation ingredients (i.e., viscosity enhancing agents, plasticizers, preservatives, active drugs, etc.) can be simply mixed with the LCHC dispersion using a mechanical stirrer, followed by homogenization of the mixture. If desired, heated oil and water phases can be prepared separately, combined, and the resultant blend allowed to cool to room temperature with constant agitation. Formulations, prepared utilizing the present LCHC material, rub-in smoothly on the skin, and rapidly dry to form Uniform, transparent, invisible, flexible, and non-tacky and non-oily films.

Active ingredients can be selected from a wide variety of cosmetics, pharmaceuticals, insecticides, herbicides, rodenticides, fungicides, pigments, insect repellents or fragrances.

The following examples are provided to more fully illustrate the utility of the LCHC material in topical formulations, and should not be construed as limiting the scope thereof.

A. Antihistamine/Skin Protectant Lotion

The procedure of Example 1 was repeated to produce an LCHC cake that contained 15% LCC. 24.1 grams of this cake was taken in 15 grams of water, and then thoroughly mixed with 5.0 grams of diphenhydramine hydrochloride, and 0.5 grams of glycerin. The mixture was then homogenized to produce a white stable lotion product. This product rubs-in smoothly on the skin, and can be used for relief from itching due to minor skin irritations.

B. Anti-acne Lotion and Cream

An LCHC cake containing 12.4% of LCC was prepared according to the procedure of Example 1. To 28.3 grams of this cake, equivalent to about 3.5 grams of the LCC, was added about 43.7 grams of water. The mixture was stirred until a homogeneous suspension was formed. While continuing stirring, 0.3 grams of the cross-linked polyacrylic acid (Carbomer 934P, Goodrich), 0.15 grams of methyl paraben, and 0.10 grams of propyl paraben, were added to the LCHC mixture. Once the Carbomer was completely dissolved, 14.3 grams of 30% benzoyl peroxide U.S.P. was added. The mixture was then homogenized to produce a homogeneous dispersion. At this stage, while continuing stirring, 13.0 grams of glycerin was added to the mixture. After stirring the mixture for about an hour, 0.3. grams of triethanolamine was added. An immediate increase in the viscosity occurred. The lotion product, thus obtained, was stirred for an additional one to one and a half hour, and then homogenized. The product is cosmetically superior and elegant. Being 100% water based, the product, when applied on the skin, rapidly dries to form uniform, transparent, virtually invisible and non-oily films. The oil-based systems tend to aggravate acne conditions.

A cream product, exhibiting similar cosmetic elegancy and characteristics as were observed with the lotion product, was prepared using the same procedure as described above. The compositions of the various ingredients were: LCHC 32.0 grams (corresponded to 5.0% LCC), Carbomer 934P 0.5 grams, triethanolamine 0.5 grams, methyl paraben 0.15 grams, propyl paraben 0.10 grams, benzoyl peroxide 14.3 grams, glycerin 14.0 grams, and water to 100 grams.

C. Anti-inflammatory Cream 48.1 grams of the LCHC cake (equivalent to about 7.5 grams of the LCC), 0.5 grams of the Carbomer 934P, 0.15 grams of methyl paraben, and 0.10 grams of propyl paraben were combined with 39.6 grams of water. The mixture was stirred to produce a homogeneous dispersion. 10.0 grams of glycerin and 1.0 grams of hydrocortisone were then added to the mixture with stirring. Further stirring for an additional hour, followed by homogenization produced a 1% hydrocortisone cream product.

D. External Analgesic Cream

A mixture containing 22.4 grams of LCHC cake (equivalent to 3.5 grams of the LCC), 1.0 grams of Tween 20, 0.25 grams of Carbomer 934P, 0.15 grams of methyl paraben, 0.10 grams of propyl paraben, and 25.6 grams water, was stirred until a homogeneous dispersion was formed. To this, while continuing stirring, a solution that comprised 10.0 grams of menthol and 30.0 grams of methyl salicylate, was added. To the resulting mixture were then added 10.0 grams of glycerin, 0.25 grams of triethanolamine, and 0.25 grams of hydroxypropylmethylcellulose (Methocel®Krm, Dow Chemicals), in the order written. The resulting cream product was stirred for an additional hour and then homogenized. It was stored in a half or one ounce aluminum tube that had a lining of a phenolic epoxy polymer. The product is physically and chemically stable, and rubs-in smoothly on the skin to produce a monolithic non-greasy film having prolonged release characteristics.

E. Spray System for Perfumes

A cosmetically elegant spray formulation was prepared by homogenizing a dispersion that comprised 22.4 grams of LCHC cake (equivalent to 3.0 grams of LCC), 0.15 grams of methyl paraben, 0.10 grams of propyl paraben, 0.5 grams of Tween 20, 0.1 grams of Carbomer 934P, 0.1 grams of triethanolamine, 10.0 grams of glycerin, and 1.0 to 3.0 grams or more of a perfume. The product can be sprayed utilizing a standard pump spray package assembly.

What is claimed is:

1. A low crystallinity powdered cellulosic material having a degree of polymerization within the range of 35 to 180 and a degree of crystallinity within the range of 15% to 45% derived from dehydrating a low crystallinity cellulosic cake material prepared by reacting cellulosic material with 85%–99% concentrated phosphoric acid in a sequential temperature reaction with a first sequential step being at a temperature within the range of 15° C. to 30° C. for up to one hour and a second sequential step being within the range of 45° C. to 75° C. for from about 2.0 hours to about 10.5 hours, with the weight ratio of cellulose to phosphoric acid being from 1:2 to 1:20 and then separating the low crystallinity cellulosic material to provide a cake which is reactivated with an anhydrous organic solvent followed by drying and grinding to provide a low crystallinity powdered cellulosic material having a particle size of less than 1.00 μm.

2. A low crystallinity beaded cellulosic material having a degree of polymerization within the range of 35 to 180 and a degree of crystallinity within the range of 15% to 45% prepared from reacting a cellulosic material with 85%–99% concentrated phosphoric acid in a sequential temperature reaction with a first sequential step being at a temperature within the range of 15° C. to 30° C. for up to one hour and a second sequential step being within the range of 45° C. to 75° C. for from about 2.0 hours to about 10.5 hours, with the weight ratio of cellulose to phosphoric acid being from 1:2 to 1:20 to provide a low crystallinity cellulosic product wherein the particles have a size of less than 1.00 μm which is then separated, water dispersed, and then spray dried.

3. The product of claim 2 which is prepared using a colloidal dispersion that contains from about 1% to about 8% concentration of low crystallinity cellulosic material.

4. The product of claim 2 which is prepared using a colloidal dispersion that contains from about 3% to about 6% by weight concentration of colloidally dispersed low crystallinity cellulosic material.

5. The product of claim 2 which has a primary particle size for the majority of said particles of from 0.2 μm to about 0.5 μm.

6. The product of claim 5 wherein the particles are spherical.

7. A formulary product selected from the group consisting of pharmaceutic products, cosmetic products, veterinary products, agricultural products and personal care products comprising:

a product active and as an excipient-effective amount of low crystallinity cellulosic material having a degree of polymerization within the range of 35 to 180 and a degree of crystallinity within the range of 15% to 45% obtained by reacting said cellulosic material within the range of 15° C. to 30° C. for up to one hour and a second sequential step being within the range of 45° C. to 75° C. for from about 2.0 hours to about 10.5 hours with 85% to 99% concentrated phosphoric acid in a sequential temperature reaction to provide particles of a size less than 1.00 μm.

8. The product of claim 7 wherein the formulary product is a pharmaceutic product.

9. The product of claim 7 when the formulary product is a cosmetic product.

10. The product of claim 7 wherein the formulary product is a personal care product.

* * * * *